United States Patent [19]
Menschik et al.

[11] 4,096,257
[45] Jun. 20, 1978

[54] SUBSTITUTED IMIDAZO [1,2-d]-AS-TRIAZINES

[75] Inventors: Judith Menschik, Tappan, N.Y.; Rolf Paul, River Vale, N.J.

[73] Assignee: American Cyanamid Company, Stamford, Conn.

[21] Appl. No.: 799,837

[22] Filed: May 23, 1977

[51] Int. Cl.$^2$ .................... A61K 31/53; C07D 471/04
[52] U.S. Cl. ...................................... 424/249; 544/184
[58] Field of Search .......................... 544/184; 424/249

[56] References Cited
U.S. PATENT DOCUMENTS 3,941,785   3/1976   Clarke et al. .................. 544/184

Primary Examiner—John M. Ford
Attorney, Agent, or Firm—Edward A. Conroy, Jr.

[57] ABSTRACT

This disclosure describes 5-n-propyl-imidazo[1,2-d]-as-triazin-8(7H)-one and 5-phenyl-imidazo[1,2-d]-as-triazin-8(7H)-one which are useful as anti-asthmatic agents and as inhibitors of the enzyme cyclic-AMP phosphodiesterase.

5 Claims, No Drawings

SUBSTITUTED IMIDAZO [1,2-d]-AS-TRIAZINES

BRIEF SUMMARY OF THE INVENTION

This invention relates to new organic compounds and, more particularly, is concerned with novel substituted imidazo[1,2-d]-as-triazin-8(7H)-ones which may be represented by the following structural formula:

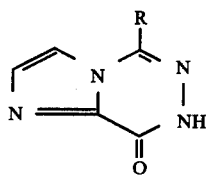

wherein R is n-propyl or phenyl. The invention also includes novel compositions of matter containing the above-defined compounds and the method of meliorating psoriasis and/or asthma in mammals therewith.

DETAILED DESCRIPTION OF THE INVENTION

The novel compounds of the present invention are active in inhibiting the enzyme cyclic-AMP phosphodiesterase which is responsible for the metabolism of cyclic adenosiue monophosphate which is usually simply referred to as cyclic AMP. As such, they are useful in the treatment of psoriasis, a disease in which the epidermal cyclic AMP levels are reported to be decreased. Also as such, they are useful in the treatment of asthma, since elevated levels of cyclic AMP in most cells are reported to inhibit the release of histamine and other mediators and since elevated levels of cyclic AMP in bronchial smooth muscle are reported to cause bronchodilation. See Ann. Reports in Medicinal Chem., Vol. 10, 197 (1975).

The inhibition of phosphodiesterase is determined by the mouse skin phosphodiesterase (PDE) inhibition test as follows:

Preparation of Mouse Skin PDE

Hairless mice (Jackson Laboratories), 3-4 months old are killed by cervical dislocation and their skins removed. Epidermal slices are taken at a thickness of 0.2 mm. The slices are weighed and homogenized at 100 mg./ml. in ice-cold tris-HCl buffer (0.04M, pH 8, containing 0.005M $MgCl_2$). Homogenates are centrifuged at 17,000 × gravity for 30 minutes. The supernatants are divided into aliquots which are stored at −20° C. Dilutions of the PDE are made with tris-HCl buffer just prior to use.

Anion Exchange Resin

AG1-X2 ®, 200-400 mesh (a polystyrene anionic exchange resin 8% cross linked from Bio-Rad Lab.) is washed with 0.5N HCl, 0.5N NaOH, 0.5N HCl and repeatedly with double distilled water to pH 5. The resin is allowed to settle and 2 volumes of water are added to one volume of settled resin.

Purification of $^3H$ Cyclic AMP $^3H$-Cyclic AMP (21 c/m mole, Schwarz-Mann Inc.) is purified by addition of 0.1 to 0.2 ml. of stock (in 50% ethanol) to 5 ml. of anion exchange resin and 0.4 ml. of tris-HCl buffer. The mixture is vortexed, cenrifuged at 1200 × gravity for 5 minutes and the supernatant is discarded. The resin is washed in the same manner eight more times with two volumes of tris-HCl buffer. Resin bound $^3H$-cyclic AMP is eluted by two successive washings with 4 ml. of 0.025N HCl (resin pH = 2.0). After centrifugation, the pooled acid washes containing $^3H$-cyclic AMP are aliquoted and lyophilized. The material is stored dry at −20° C. and reconstituted with tris-HCl buffer just prior to use with a volume sufficient to give approximately 200,000 CPM/0.1 ml.

PDE Assay

PDE activity is measured by the method of W. J. Thompson and N. N. Appleman, Biochemistry 10, 311 (1971). Assays are conducted in 12 × 75 mm. polypropylene test tubes. The reaction mixture consists of $^3H$-cyclic AMP (200,000 CPM), unlabeled cyclic AMP, PDE (100 ug. protein) and test compounds which are prepared by dissolving the compounds in methanol at a concentration of 10 mg./ml. and then dilution in tris-HCl buffer. Final concentration of the test compounds in the incubation mixture is 10 ug./ml. The total volume of the incubation mixture is increased to 0.4 ml. with tris-HCl buffer containing 3.75 millimoles of 2-mercaptoethanol. The enzyme is incubated for 10 minutes at room temperature in the presence of the test compounds or buffer prior to the addition of the mixture of $^3H$-cyclic AMP and unlabeled cyclic AMP. Reactions are run at 30° C. for 15 minutes and then terminated by immersing in acetone-dry ice until frozen, followed by boiling for 3 minutes. Tubes are cooled to room temperarture. $^3H$-5′ AMP, formed in the reaction is converted to $^3H$-adenosine by the addition of 0.1 ml. of a solution of 5′-nucleotidase [16 ug./ml. in double distilled water Crotalus venom (Sigma Chemicals)] to the tubes which are incubated for 20 minutes at room temperature. This reaction is ended by the addition of one ml. of ice cold, stirred resin slurry which binds charged nucleotides (including $^3H$-cyclic AMP) but not $^3H$-adenosine. Tubes are vortexed and immersed in an ice bath for 15 minutes and then centrifuged at 1200 × gravity for 5 minutes. A 0.5 ml. portion is taken from each, placed in liquid scintillation vials with 10 ml. of Ready-Solv VI (Beckman Ind.) and counted for radio activity. Assay "blanks", determined with assay buffer substituted for PDE are less than 1% of total $^3H$-cyclic AMP added when $^3H$-cyclic AMP is purified as indicated.

Criterion for Activity as Inhibitor of Skin Phosphodiesterase

A compound is considered active if it inhibits more than theophylline, that is, to 50% of control at 1 mM concentration of compound, or to 80% of control of 0.05 mM concentration of compound. The results with the novel compounds of the present invention on inhibition of phosphodiesterase are recorded in Table I below.

TABLE I

| Compound | Mouse Skin Phosphodiesterase |
| --- | --- |
| 5-n-Propyl-imidazo[1,2-d]-as-triazin-8(7H)-one | Active |
| 5-Phenyl-imidazo[1,2-d]-as-triazin-8(7H)-one | Active |

The novel compounds of the present invention have thus been found to be highly useful for inhibiting the enzyme phosphodiesterase in mammals when administered in amounts ranging from about 1.0 milligram to about 100.0 mg. per kilogram of body weight per day. A preferred dosage regimen for optimum results would be from about 5.0 mg. to about 50.0 mg. per kilogram of body weight per day, and such dosage units are employed that a total of from about 0.35 gram to about 3.5 gram of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compounds may be administered in any convenient manner such as by the oral, intravenous, intramuscular, or subcutaneous routes, and also by inhalation therapy including aerosol sprays.

Compositions according to the present invention having the desired clarity, stability and adaptability for parenteral use are obtained by dissolving from 0.10 to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 250 and 500 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

Preparation of
5-n-propyl-imidazo[1,2-d]-as-triazin-8(7H)-one

A mixture of 37.0 gm. of 2-imidazolecarboxylic acid hydrazide, prepared by the method of U.S. Pat. No. 3,600,399, 2.5 liters of ethanol and 325 ml. of trimethylorthobutyrate is refluxed overnight and evaporated to a solid. This solid is ground, added to 400 ml. of diphenyl ether and heated in an oil bath at 220°–245° C. for 30 minutes. The mixture is cooled to room temperature and crystallized by the addition of 100 ml. of petroleum ether. The solid is collected, washed twice with petroleum ether, recrystallized from 300 ml. of a hot mixture of ethanol and methanol and treated with charcoal giving 53.5 gm. of the desired final product, m.p. 153°–159° C.

EXAMPLE 2

Preparation of
5-phenyl-imidazo[1,2-d]-as-triazin-8(7H)-one

A 2.6 gm. portion of 2-imidazolecarboxylic acid hydrazide is added to 200 ml. of ethanol. To this is added 20 ml. of trimethylorthobenzoate. The mixture is refluxed for 31 hours, then the solvents are evaporated giving a white solid which is washed twice with diethyl ether giving 3.0 gm. of white solid. This solid is combined with 50 ml. of diphenyl ether and heated with stirring in an oil bath at 265°–275° C. for 10 minutes. The mixture is cooled, petroleum ether is added and the mixture is filtered. The solid is washed twice with hot petroleum ether, giving 1.4 gm. of the desired product as a light tan solid, m.p. 292°–295° C.

EXAMPLE 3

Preparation of 50 mg. Tablets

| Per Tablet | | Per 10,000 Tablets |
|---|---|---|
| 0.050 gm. | 5-n-propyl-imidazo-[1,2-d]-as-triazin-8(7H)-one | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 5-n-propyl-imidazo[1,2-d]-as-triazin-8(7H)-one, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 4

Preparation of Oral Suspension

| Ingredient | Amount |
|---|---|
| 5-phenyl-imidazo[1,2-d]-as-triazin-8(7H)-one | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water   qs to | 100 ml. |

The sorbitol solution is added to 40 ml. of distilled water and the 5-phenyl-imidazo[1,2-d]-as-triazin-8(7H)-one is suspended therein. The saccharin, sodium benzoate, flavor and dye are added and dissolved. The volume is adjusted to 100 ml. with distilled water. Each ml. of syrup contains 5 mg. of 5-phenyl-imidazo[1,2-d]-as-triazin-8(7H)-one.

EXAMPLE 5

Preparation of Parenteral Solution

In a solution of 700 ml. of propylene glycol and 200 ml. of water for injection is suspended 20.0 grams of 5-n-propyl-imidazo[1,2-d]-as-triazin-8(7H)-one with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 6

Preparation of Aerosol Spray

A suspension is prepared of:

| | |
|---|---|
| 5-phenyl-imidazo[1,2-d]-as-triazin-8(7H)-one | 400 mg. |
| Dichlorodifluoromethane | 100 ml. |
| Sorbitan trioleate | 6.9 mg. |

The active ingredient and sorbitan trioleate are placed in a beaker and the dichlorodifluoromethane is added at −40° C. whereupon a suspension is formed. The mixture is sonified, that is, treated with a Sonifier, manufactured by the Branson Sonic Power Co. of Danbury, Connecticut, as model LS-75 at a current input of 9 amperes for 2 minutes. Additional cold dichlorodifluoromethane is added as necessary to keep the volume at 100 ml. The mixture is uniformly dispersed, and has increased stability resulting from the sonification. Each of six 19 ml. stainless steel containers are filled with 15 ml. of the cold mixture, then valves are inserted and sealed in place. On warming after storage, the 5-phenyl-imidazo[1,2-d]-as-triazin-8(7H)-one remains dispersed and, after merely casual shaking gives uniform doses of finely divided drug.

We claim:

1. 5-n-Propyl-imidazo[1,2-d]-as-triazin-8(7H)-one.
2. 5-Phenyl-imidazo[1,2-d]-as-triazin-8(7H)-one.
3. The method of meliorating asthma in a mammal which comprises administering internally to said mammal an effective amount of 5-n-propyl-imidazo[1,2-d]-as-triazin-8(7H)-one or 5-phenyl imidazo[1,2-d]-as-triazin-8(7H)-one.
4. A therapeutic composition in dosage unit form useful for meliorating asthma in mammals comprising from about one milligram to about one hundred milligrams per kilogram of body weight per daily dosage unit, in association with a pharmaceutical carrier, of 5-n-propyl-imidazo[1,2-d]-as-triazin-8(7H)-one.
5. The process of preparing a compound of the formula:

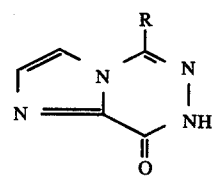

wherein R is n-propyl or phenyl which comprises heating a compound of the formula:

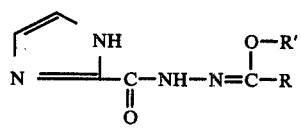

wherein R' is methyl or ethyl and R is as hereinabove defined in a non-polar high boiling organic solvent at a temperature of 220°–295° C. for a period of time sufficient for a substantial degree of ring closure to occur.

* * * * *

UNITED STATES PATENT OFFICE
CERTIFICATE OF CORRECTION

Patent No. 4,096,257　　　　　　　Dated June 20, 1978

Inventor(s) Judith Menschik and Rolf Paul

It is certified that error appears in the above-identified patent and that said Letters Patent are hereby corrected as shown below:

Column 6, line 41, Claim 4, after "5-n-propyl-imidazo[1,2-d]--as-triazin-8(7H)-one" add -- or 5-phenyl-imidazo[1,2-d]--as-triazin-8(7H)-one. --

Signed and Sealed this

Second Day of January 1979

[SEAL]

Attest:

RUTH C. MASON
Attesting Officer

DONALD W. BANNER
Commissioner of Patents and Trademarks